US010274570B2

United States Patent
Suh et al.

(10) Patent No.: US 10,274,570 B2
(45) Date of Patent: Apr. 30, 2019

(54) PHANTOM FOR QUALITY ASSURANCE OF MAGNETIC RESONANCE IMAGING AND COMPUTED TOMOGRAPHY FOR MULTI-ARTIFACT CORRECTION

(71) Applicant: THE CATHOLIC UNIVERSITY OF KOREA INDUSTRY-ACADEMIC COOPERATION FOUNDATION, Seoul (KR)

(72) Inventors: Tae-Suk Suh, Seoul (KR); Min-Young Lee, Seoul (KR); Kyu-Ho Song, Gyeonggi-do (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 410 days.

(21) Appl. No.: 15/286,992

(22) Filed: Oct. 6, 2016

(65) Prior Publication Data
US 2017/0336490 A1 Nov. 23, 2017

(30) Foreign Application Priority Data
May 17, 2016 (KR) .................. 10-2016-0060104

(51) Int. Cl.
*G01V 3/00* (2006.01)
*G01R 33/58* (2006.01)
(Continued)

(52) U.S. Cl.
CPC .............. *G01R 33/58* (2013.01); *A61B 6/032* (2013.01); *A61B 6/583* (2013.01); *G01R 33/4812* (2013.01)

(58) Field of Classification Search
CPC ..................................................... G01R 33/58
(Continued)

(56) References Cited

U.S. PATENT DOCUMENTS

2015/0309149 A1* 10/2015 Holdsworth ........... G01R 33/58
324/309
2015/0323639 A1 11/2015 Boss
(Continued)

FOREIGN PATENT DOCUMENTS

| KR | 1020080056553 | 5/2010 |
|---|---|---|
| KR | 100961892 | 6/2010 |

(Continued)

*Primary Examiner* — Louis M Arana
(74) *Attorney, Agent, or Firm* — Allen, Dyer, Doppelt + Gilchrist, P.A. Attorneys at Law

(57) ABSTRACT

The present invention relates to a phantom for quality assurance of magnetic resonance imaging (MRI) and computed tomography (CT) for multi-artifact correction. An aspect of the present invention provides a phantom capable of simultaneously evaluating performance of magnetic resonance imaging (MRI) and computed tomography (CT), the phantom including: a first hemispheric container; and a second hemispheric container which has the same structure and the same size as the first container, in which the first container and the second container are connected by being in direct contact with each other so as to form a symmetrical structure, each of the first container and the second container includes a teeth retainer into which a plurality of teeth mimics, which mimics teeth of a body, is inserted, and an insertion hole into which at least one bone mimic is inserted, and an interior of each of the first container and the second container is filled with at least one solution that mimics a brain metabolite.

10 Claims, 2 Drawing Sheets

(51) Int. Cl.
  *A61B 6/03*    (2006.01)
  *A61B 6/00*    (2006.01)
  *G01R 33/48*   (2006.01)

(58) Field of Classification Search
  USPC .................................................. 324/308, 321
  See application file for complete search history.

(56) References Cited

U.S. PATENT DOCUMENTS

2016/0282439 A1* 9/2016 Choe ....................... G01R 33/58
2018/0242944 A1* 8/2018 Uber, III ................ A61B 6/032

FOREIGN PATENT DOCUMENTS

KR    20150099948    9/2015
KR      101602928    3/2016

* cited by examiner

[FIG. 1]
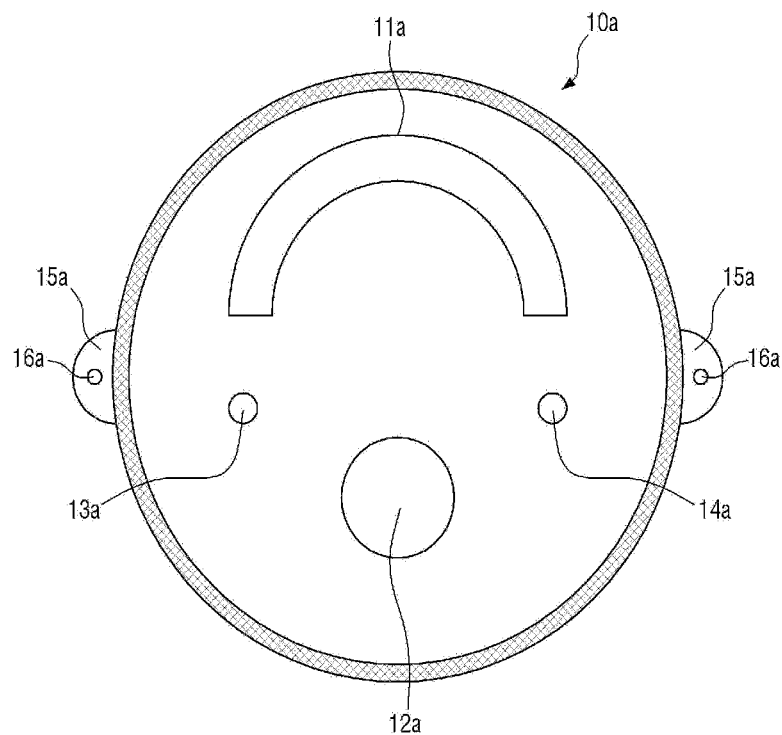
[FIG. 2]
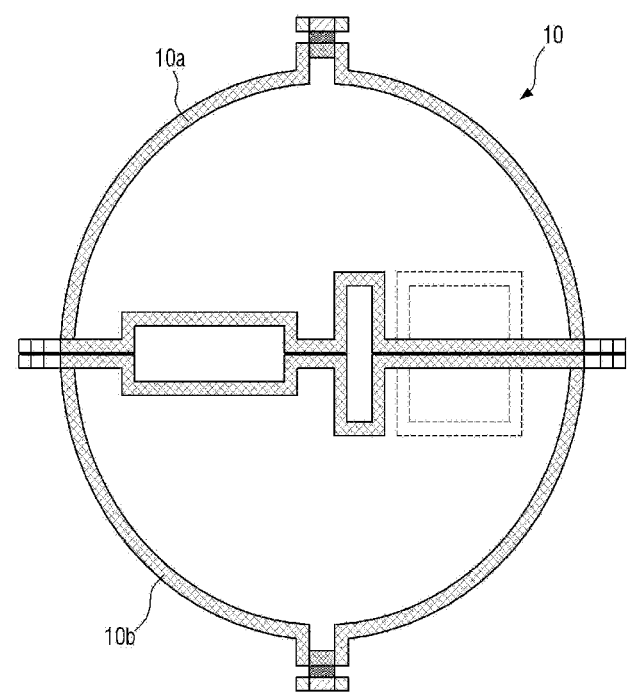

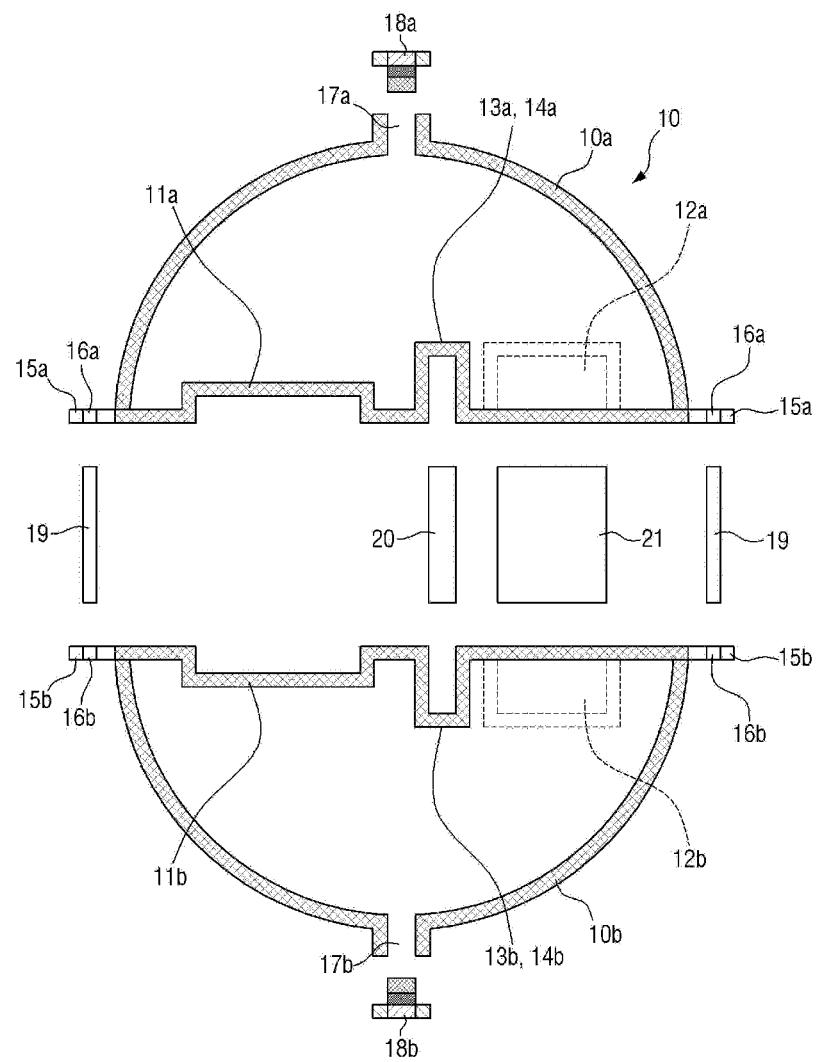
[FIG. 3]

PHANTOM FOR QUALITY ASSURANCE OF MAGNETIC RESONANCE IMAGING AND COMPUTED TOMOGRAPHY FOR MULTI-ARTIFACT CORRECTION

CROSS-REFERENCE TO RELATED APPLICATIONS

This application claims the priority of Korean Patent Application No. 2016-60104 filed on May 17, 2016, in the Korean Intellectual Property Office, the disclosure of which is incorporated herein by reference.

BACKGROUND

Field

The present invention relates to a phantom for quality assurance of magnetic resonance imaging (MRI) and computed tomography (CT) for multi-artifact correction.

That is, the present invention proposes a phantom for improving efficiency of quality assurance attempted to correct an artifact of a human magnetic resonance imaging (MRI) system and a human computed tomography (CT) system.

In particular, the present invention relates to a fusion phantom capable of simultaneously performing quality assurance of the two imaging systems within an acceptable range of a quality evaluation, by assessing performance ability of magnetic resonance imaging and computed tomography and recognizing a consistent allowable error range or whether or not the presence of an artifact.

Description of the Related Art

Magnetic resonance imaging (MRI) is a representative imaging technique capable of measuring a brain function of a human, and magnetic resonance spectroscopy (MRS), which may detect chemical components of brain tissues by providing structural images for providing various image contrasts, is widely used.

The magnetic resonance imaging (MRI) is one of the imaging technologies and uses a nuclear magnetic resonance principle. That is, when a magnetic resonance imaging device, which generates a magnetic field, is put into a human body, and high frequency waves are generated, hydrogen atoms in the body resonate. In this case, a difference in signals, which occurs when the hydrogen atoms resonate, is measured, and the measurement result is reconstructed and visualized by means of a computer, thereby making magnetic resonance images.

Unlike an X-ray computer tomography (CT) which is harmful to a human body because the X-ray computer tomography uses X-rays, the magnetic resonance imaging is characterized by being harmless to the human body, and the CT mainly provides cross-sectional images, but the MRI has an advantage in that the MRI is free to a direction.

In order to evaluate performance of the magnetic resonance imaging system, an ACR (American college of radiology-magnetic resonance imaging) phantom for human equipment and an AAPM (American association of physicists in medicine) phantom for human equipment have been generally used.

That is, in order to precisely and accurately analyze and evaluate image interpretation and clinical systems, performance evaluation of the human magnetic resonance imaging is performed based on a standard protocol.

A phantom, which is used to evaluate performance of the human magnetic resonance imaging system, is used to predict an abnormality (error) in a case in which an event occurs beyond an allowable error range and a limit error range of the human magnetic resonance system, and to propose, approach, and solve parts having errors by bringing a focus on diagnosis.

Whether the magnetic resonance system is normally operated in connection with hardware in the human magnetic resonance imaging system is checked, and in a case in which the check result goes beyond the allowable error range that occurs through daily, weekly, and monthly quality assurance, related elements are inspected and analyzed so that a problem associated with a diagnosis error may be solved.

The existing ACR-MRI (American college of radiology-magnetic resonance imaging) phantom and the existing ACR-CT phantom, and the existing AAPM-CT (American association of physicists in medicine-computed tomography) phantom perform evaluation of the magnetic resonance imaging and the computed tomography based on the existing protocol and the existing parameter in order to perform the image interpretation including high quality of the clinical systems.

The phantoms, which are used to evaluate performance, predict that there will be an abnormality in a case in which the event goes beyond the allowable error range of the magnetic resonance system and an artifact is found, and a system administrator and operator proposes, approaches, and solves predicted ranges and parts.

Whether the magnetic resonance system and the computed tomography system are normally operated in connection with hardware and hardware accessories is checked, and elements associated with the found artifact are solved by yearly, monthly, and daily quality assurance.

The magnetic resonance imaging system is an imaging system which is most widely used to find minute boundary portions of fine tissues by performing chemical investigation and quantification, and obtaining anatomical images and histological images.

The magnetic resonance imaging is also used as a tool for providing information about metabolism in the body, and analysis of spectrums is also used through the magnetic resonance spectroscopy.

In addition, the magnetic resonance imaging finds an early diagnosis and various diseases, together with changes of inside and outside cells, based on the analysis of the spectrums, and in order to eliminate a risk of the existing radiation impairment, the magnetic resonance imaging may visualize tissues of the human body by using a radio resonance frequency and a magnetic field.

An imaging system using X-rays may obtain only information about cross sections of the human body, and cannot obtain information about cross sections other than the cross sections of the human body, but the magnetic resonance imaging may substantially obtain a diagnosis region and diagnosis information which are expanded based on imaging technologies such as T1, T2, perfusion, diffusion, and a blood stream. In particular, the magnetic resonance imaging system provides the best resolution of soft tissues in comparison with other imaging systems available up to now.

In addition, the magnetic resonance imaging is a method of distributing and distinguishing a difference in concentration between various metabolites of the human body, and the magnetic resonance imaging may evaluate treatment influences when treating diseases as well as an early diagnosis, and detect positions where diseases occur based on a change in metabolite.

Meanwhile, there is a limitation in that quality assurance of the existing ACR-MR phantom, AAPM-CT phantom, and ACR-CT phantom is performed based on a standard instead of artifact correction.

For example, the magnetic resonance imaging phantom may evaluate geometric accuracy, space resolution, accuracy of a slice position, image intensity, contrast resolution, and signal percentage, but only the magnetic resonance imaging may be restrictively evaluated, and an artifact cannot be evaluated and inner metabolites cannot be evaluated quantitively.

In addition, in a case in which a patient having a head and neck disease is subjected to the magnetic resonance imaging and the computed tomography in a state in which a dental prosthesis (metal) is inserted or retained in the patient, there is a problem in that unnecessary information is obtained in an image during a reconstruction process, and as a result, a treatment is carried out based on an inaccurate scheme.

Therefore, there is an acute need for a phantom capable of solving the aforementioned problem.

LITERATURE OF RELATED ART

Patent Document (Patent Document 1) Korean Patent No. 10-0961892

SUMMARY

The present invention relates to a phantom for quality assurance of magnetic resonance imaging (MRI) and computed tomography (CT) for multi-artifact correction, and an object of the present invention is to provide a user with a phantom for improving efficiency of quality assurance which is attempted to correct an artifact of a human magnetic resonance imaging (MRI) system and a human computed tomography (CT) system.

In particular, an object of the present invention is to provide a user with a fusion phantom capable of simultaneously performing quality assurance of the two imaging systems within an acceptable range of a quality evaluation, by assessing performance ability of magnetic resonance imaging and computed tomography and recognizing a consistent allowable error range or whether or not the presence of an artifact.

Technical problems to be solved by the present invention are not limited to the aforementioned technical problem, and other technical problems, which are not mentioned above, may be clearly understood from the following descriptions by those skilled in the art to which the present invention pertains.

An exemplary embodiment of the present invention provides a phantom capable of simultaneously evaluating performance of magnetic resonance imaging (MRI) and computed tomography (CT), the phantom including: a first hemispheric container; and a second hemispheric container which has the same structure and the same size as the first container, in which the first container and the second container are connected by being in direct contact with each other so as to form a symmetry structure, each of the first container and the second container includes a teeth retainer into which a plurality of teeth mimics, which mimics teeth of a body, is inserted, and an insertion hole into which at least one bone mimic is inserted, and an interior of each of the first container and the second container is filled with at least one solution that mimics a brain metabolite.

In addition, a first of first surface of the first container, which has a largest area, and a first of second surface of the second container, which has a largest area, may be in direct contact with each other so as to form a symmetrical structure, each of the first container and the second container may further include an inlet which is positioned at a side opposite to the first of first surface or the first of second surface such that at least one solution, which mimics the brain metabolite, is injected through the inlet, and the inlet may be opened and closed by a closure.

In addition, the teeth retainers and the insertion holes may be formed on the first of first surface and the first of second surface.

In addition, the interiors of the first container and the second container may be filled first with copper sulfate ($CuSO_4$; 0.7 g/L).

In addition, the interiors of the first container and the second container may further include N-acetyl-Laspartic acid; Creatine hydrate; Cr; 10.0 mM, Choline chloride; Cho; 3.0 mM, Myo-inositol; NAA; 12.5 mM, L-Glutamic acid; Glu; 12.5 mM, DL-lactic acid; Lac; 5.0 mM, 4-Aminobutyric acid; GABA; 10.0 mM, ml; 7.5 mM, L-Alanine; Al; 10.0 mM, L-Glutamine; Gln; 12.5 mM, Taurine; Tau; 6.0 mM.

In addition, a mixture ratio between monopotassium phosphate ($KH_2PO_4$; 32 mM) and tripotassium phosphate ($K_3PO_4$; 18 mM) may be adjusted to allow pH in the first container and the second container to be equal to pH of the body.

In addition, the plurality of teeth mimics may include a titanium material or teeth.

In addition, the teeth retainer may be made of a thermoplastic plastic material in order to fix a position of the plurality of inserted teeth mimics.

In addition, positions of the plurality of teeth mimics inserted into the teeth retainer may be changed by using a nature of the thermoplastic plastic in which the thermoplastic plastic is plastically deformed when the thermoplastic plastic is heated, and the thermoplastic plastic is reversibly hardened when the thermoplastic plastic is cooled.

In addition, fastening holes may be formed in the first container and the second container, respectively, and the first container and the second container may be connected by being in direct contact with each other by means of a coupler that penetrates the fastening holes.

The present invention relates to a phantom for quality assurance of magnetic resonance imaging (MRI) and computed tomography (CT) for multi-artifact correction, and the present invention may provide a user with a phantom for improving efficiency of quality assurance which is attempted to correct an artifact of a human magnetic resonance imaging (MRI) system and a human computed tomography (CT) system.

In particular, the present invention may provide a user with the fusion phantom capable of simultaneously performing quality assurance of the two imaging systems within an acceptable range of a quality evaluation, by assessing performance ability of magnetic resonance imaging and computed tomography and recognizing a consistent allowable error range or whether or not the presence of an artifact.

In addition, according to the fusion phantom for the magnetic resonance imaging and the computed tomography of the present invention, in order to reproduce an actual artifact at upper and lower ends based on the evaluation slice for evaluating geometric cross section accuracy at the middle in the two hemispheric containers, teeth extracted from patients and dental implants made of a titanium material, which is a biocompatible alloy currently used in dental clinics, may be inserted into the phantom.

In addition, this material may be supplemented by a number of materials, an image of teeth of a child may be implemented, and additional insertion may be possible. Typically, an ordinary person has 28 teeth except for wisdom teeth, and thus a material configured with non-limited teeth is inserted so that 14 upper teeth and 14 lower teeth may be implemented.

In addition, the teeth and the dental implants may be inserted, fixed, and attached to a center of acrylic, and desired teeth made of different substances may be inserted.

In addition, the next teeth is made of thermoplastic resin so as to be fixed at a desired position, and the next resin is inserted into a teeth retainer by using a feature that the next resin is easy to use because the resin is deformed by heat, and the resin may be deformed in a desired shape and a direction, and as a result, it is possible to completely make a retainer having a diameter of 1.5 cm and a height of 2 cm and a teeth model by surrounding the teeth, the dental implants, and the teeth made of a different material with the thermoplastic resin in a state in which the teeth, the dental implants, and the teeth made of a different material are deformed by heat, and by bringing the teeth, the dental implants, and the teeth made of a different material into close contact with the retainer.

A shape of the teeth retainer of the present invention may be modified, and an open mouth (a mouth is opened) and a closed mouth (the mouth is closed) may be implemented.

Therefore, the present invention may not only perform a diagnosis, but also mimics a patient having a dental prosthesis, a patient having no dental prosthesis, a patient with an opened mouth, or a patient with a closed mouth when treating a radiotherapy.

Here, the thermoplastic resin for fixing the teeth has a characteristic of substances of actual tissues of the human body; thus, may be suitable to use because the thermoplastic resin is a non-magnetic substance that does not have an effect on the process of obtaining magnetic resonance images.

In addition, according to the fusion phantom for magnetic resonance imaging and computed tomography according to the present invention, the column made of a Teflon material which may be used to check a slide position, is inserted into the two spherical containers, and as a result, it is possible to evaluate a position of a height of 2 cm at the teeth retainers and a position of a height of 4 cm at the Teflon column.

In addition, in order to allow a voxel position to be freely set in the containers, a metabolite quantitative evaluation is performed by setting a position at a hemispheric center and positioning the voxels at the upper and lower ends, thereby, simultaneously obtaining the voxels at the upper and lower ends and improving temporal efficiency.

In addition, since a size of the phantom is similar to a size of the human brain, and the phantom is easy to evaluate the metabolite, and may reduce a chemical shift artifact due to a small acrylic thickness of 5 mm between the exterior and the interior.

In addition, a quantitative evaluation using a single volume magnetic resonance spectroscopy may be possible. That is, since it is possible to adjust the amount of metabolites at the upper and lower ends of the center of the hemispheres so that a desired signal is visible when obtaining spectrums by using the magnetic resonance spectroscopy, and it is possible to accurately measure positioning accuracy of a volume of interest (in particular, a voxel positioned closest to the exterior, a voxel positioned closest to the Teflon, a voxel positioned closest to the teeth, and a voxel positioned closest to the dental implants), and for this reason, a change in chemical shift caused by the artifact may be evaluated.

Accordingly, the phantom for magnetic resonance imaging and computed tomography according to the present invention may accurately correct the artifact (in particular, the metallic artifact) and enable to perform an analysis through various quantitative evaluations when evaluating performance of the magnetic resonance imaging system and the computed tomography system. In comparison with the phantom in the related art, the metabolite may be more accurately and variously analyzed, and performance maintenance of equipment and analysis functions are simultaneously visualized; thereby obtaining images for a short period of time and improving reliability of equipment performance may be possible.

Meanwhile, the effects obtained by the present invention are not limited to the aforementioned effects, and other effects, which are not mentioned above, will be clearly understood by those skilled in the art from the following description.

BRIEF DESCRIPTION OF THE DRAWINGS

FIG. 1 is a view illustrating a specific example of a hemispheric external container proposed by the present invention;

FIG. 2 is a view illustrating a specific example of two hemispheric external containers proposed by the present invention; and FIG. 3 is a view illustrating a specific example of a fusion phantom in which the two hemispheric external containers proposed by the present invention are coupled to each other in order to simultaneously perform quality assurance of a magnetic resonance imaging system and a computed tomography system.

DETAILED DESCRIPTION OF THE PREFERRED EMBODIMENT

The present invention may have various modifications and a variety of exemplary embodiments, and thus specific exemplary embodiments will be illustrated in the drawings and described in detail in the detailed description. However, it should be understood that the present invention is not limited to the specific exemplary embodiments, and includes all of modifications, equivalents, and substitutions included in the spirit and the technical scope of the present invention. In the description of the present invention, the specific descriptions of publicly known related technologies will be omitted when it is determined that the specific descriptions may obscure the subject matter of the present invention.

The terms such as "first" and "second" may be used to describe various constituent elements, but the constituent elements should not be limited by the terms. These terms are used only to distinguish one constituent element from another constituent element.

There is a limitation in that quality assurance of the existing ACR-MR phantom, the AAPM-CT phantom, and the ACR-CT phantom which are performed based on a standard instead of artifact correction. For example, in the magnetic resonance imaging phantom, geometric accuracy, space resolution, accuracy of a position of a slice, image intensity, contrast resolution, and signal percentage may be evaluated, but only the magnetic resonance imaging may be restrictively evaluated, and has a drawback in that the magnetic resonance imaging phantom cannot evaluate an artifact and cannot quantitatively evaluate interior metabolites.

In addition, in a case in which a patient having a disease of a head and neck is subjected to the magnetic resonance imaging and the computed tomography in a state in which a dental prosthesis (metal) is inserted or retained in the patient, unnecessary information may be obtained in an image during a reconstruction process, and as a result, a treatment cannot be carried out based on an accurate scheme.

Therefore, the present invention relates to a phantom for quality assurance of magnetic resonance imaging (MRI) and computed tomography (CT) for multi-artifact correction, and an object of the present invention is to provide a user with a phantom for improving efficiency of quality assurance which is attempted to correct an artifact of a human magnetic resonance imaging (MRI) system and a human computed tomography (CT) system.

In particular, an object of the present invention is to provide a user with a fusion phantom capable of simultaneously performing quality assurance of the two imaging systems within an acceptable range of a quality evaluation, by assessing performance ability of magnetic resonance imaging and computed tomography and recognizing a consistent allowable error range or whether or not the presence of an artifact.

First, the phantom according to the present invention may correct a plurality of artifacts by improving efficiency of quality assurance, second, the phantom may correct quality of images optimized by adjusting image conditions and image variables, and third, the phantom may perform quantitative evaluations and quantitative analyses.

The present invention has been made in an effort to solve the aforementioned various problems, and two hemispheric external containers have been invented in order to simultaneously perform performance evaluations of a magnetic resonance imaging system and a computed tomography system and an evaluation of an artifact by using a single phantom. The present invention is characterized by correcting and evaluating the artifact in the magnetic resonance imaging system and the computed tomography system.

In the present invention, metabolites which are able to perform a quantitative evaluation are added into the inside of hemispheric external container.

In addition, the phantom is manufactured to have a most average size suitable to be applied to the magnetic resonance imaging system and the computed tomography system by mimicking a size of an average human brain.

The largest feature of the present invention is to correct a metallic artifact which is caused by use of a dental prosthesis and most frequently occurs among artifacts associated with the magnetic resonance imaging and the computed tomography.

In a case in which a patient having a head and neck disease is subjected to the magnetic resonance imaging and the computed tomography in a state in which the dental prosthesis (metal) is inserted or retained in the patient, there is a problem in that unnecessary information is obtained in an image during a reconstruction process, and for this reason, in the case of a cancer patient, treatment schemes may be established and treatments may be carried out based on incorrect information during a radiotherapy.

In the present invention, teeth extracted from patients and dental implants made of a titanium material, which is a biocompatible alloy currently used in dental clinics, are inserted into the phantom to solve the aforementioned problems.

That is, the teeth and the dental implants are inserted, fixed so that they are attached to a center of acrylic and desired teeth made of different substances are able to be inserted. For the next teeth, thermoplastic resin is used in order to fix at a desired position, and the next resin is inserted into a teeth retainer by using the advantages that the next resin is easy to use because the resin is deformed by heat, and the resin may be deformed in a desired shape and a desired direction, and thus, it is possible to completely make a retainer having a diameter of 1.5 cm and a height of 2 cm and a teeth model after surrounding the teeth, the dental implants, and the teeth made of a different material with the thermoplastic resin in a state in which the teeth, the dental implants, and the teeth made of a different material are deformed by heat, and by bringing the teeth, the dental implants, and the teeth made of a different material into close contact with the retainer.

A shape of the teeth retainer according to the present invention may be modified, and an open mouth (a mouth is opened) and a closed mouth (the mouth is closed) may be implemented.

Therefore, the present invention is able to not only perform a diagnosis, but also mimic a patient having a dental prosthesis during a radiotherapy, a patient having no dental prosthesis, a patient with an opened mouth, or a patient with a closed mouth. Here, the thermoplastic resin for fixing the teeth has characteristics of substances of actual tissues of the human body, and thus may be suitable to use because the thermoplastic resin is a non-magnetic substance that does not have an effect on the process of obtaining magnetic resonance images.

Next, in comparison with tests for quality assurance and artifacts of the magnetic resonance system and the computed tomography system by using the phantom in the related art, in the case of a test using the fusion phantom according to the present invention, an evaluation of the artifact of the magnetic resonance imaging and the computed tomography phantom may be obtained for a significantly short period of time, and may be accurately carried out by correcting an incorrect position accuracy and improving quality of images of the artifact.

In addition, the present invention performs a quantitative evaluation of a plurality of brain metabolites by providing a wide hemispheric voxel position, and may improve temporal efficiency and image interpretation reliability associated with the correction of the artifact within a magnetic resonance imaging and computed tomography diagnosis region by using the fusion phantom capable of performing quantitative chemical analysis.

Hereinafter, a phantom for quality assurance of magnetic resonance imaging and computed tomography for multi-artifact correction, which is proposed by the present invention, will be specifically described with reference to the drawings.

However, the present invention is not limited to the exemplary embodiment disclosed in the following, and may be embodied in many different forms.

In order to achieve the aforementioned object, a fusion phantom 10 for evaluating performance of correction of an artifact of magnetic resonance imaging and computed tomography of the present invention includes two hemispheric phantoms 10a and 10b which are positioned at upper and lower sides and have the same size and shape.

FIG. 1 is a view illustrating a specific example of a hemispheric external container proposed by the present invention, FIG. 2 is a view illustrating a specific example of two hemispheric external containers proposed by the present invention, and FIG. 3 is a view illustrating a specific example of a fusion phantom in which the two hemispheric external containers proposed by the present invention are coupled to each other in order to simultaneously perform quality assurance of a magnetic resonance imaging system and a computed tomography system.

Referring to FIGS. 1 and 3, a first hemispheric container 10a is illustrated, which has an injection port 17a which is formed in a central portion of an upper surface of the first container 10a and opened and closed by a closure, and a single inlet, which is opened and closed by a first closure 18a, is formed in the injection port 17a.

Although not illustrated in FIG. 1, a second container 10b, which corresponds to the first container 10a, also has an injection port 17b which is formed in a central portion of an upper surface of the second container 10b and opened and closed by a closure, and a single inlet, which is opened and closed by a second closure 18b, is formed in the injection port 17b, and the second container 10b has a hemispheric shape.

In addition, referring to FIGS. 2 and 3, the first container 10a and the second container 10b are positioned to face each other, two nuts 15a-15b or 16a-16b having a predetermined size and a rubber ring inserted therein are formed at both sides of each of the first and second containers, two bolts 19 are inserted into the nuts 15a-15b and 16a-16b which face each other, and as a result, two flat portions and matching portions of the first container 10a and the second container 10b may be fixed.

In addition, referring to FIGS. 1 and 3, the first container 10a has a teeth retainer 11a, a first slide groove 12a into which a slide, which is installed at the middle of the container and used to evaluate geometric accuracy, or a Teflon 21 shaped as a spinal bone is inserted, and first Teflon insertion retainers 13a and 14a into which a Teflon 20 shaped as a bone is inserted.

Referring to FIG. 3, corresponding to the first container 10a, the second container 10b also has a teeth retainer 11b, a second slide groove 12b into which a slide 21 which is installed at the middle of the container and used to evaluate geometric accuracy is inserted, and second Teflon insertion retainers 13b and 14b into which a Teflon 20 shaped as a bone is inserted.

In addition, the present invention has a technical feature in that the teeth retainers 11a and 11b into which thermoplastic resin around the teeth is inserted are disposed vertically at the same position, and formed at a single center position, thereby obtaining images of the same position when performing the magnetic resonance imaging and the computed tomography.

In addition, an interior of the first hemispheric container 10a having the single inlet, which is opened and closed by the first closure 18a and formed in the injection port 17a, may include a metabolite in order to quantitatively evaluate a brain mimic metabolite.

In other words, the first container 10a and the second container 10b are embodied to have the same shape and to be positioned at the same layer position, and an aqueous solution, which mimics a brain metabolite, may be injected into the first container 10a and the second container 10b.

According to the exemplary embodiment of the present invention, in order to inject the aqueous solution which mimics the brain metabolite, the injection ports 17a and 17b of the first container 10a and the second container 10b may be formed as an inlet having a diameter of 10 mm.

In addition, the interiors of the first container 10a and the second container 10b are filled with copper sulfate ($CuSO_4$; 0.7 g/L) by injecting the copper sulfate through the injection ports 17a and 17b, and the diluted copper sulfate solution may reduce T1 relaxation time of water.

In addition, as the solution is put into the first and second containers as described above, a high signal may be obtained when obtaining the magnetic resonance images, and a result of short time efficiency may be obtained.

Also, the voxel position is easily and accurately designated in the first container 10a and the second container 10b when the magnetic resonance imaging and spectroscopy are performed, and it is possible to reduce influences of acrylic and Teflon shaped as a bone on the artifact to the minimum extent.

That is, it is possible to obtain position accuracy of selection of a volume of interest easily, and reduce a partial volume effect.

In addition, the interiors of the first container 10a and the second container 10b are filled with solutions that mimic the brain metabolite in the hemisphere, and a temperature and pH may be adjusted to be similar to those of substances in the human body.

To adjust pH similar to that of substances of the human body, monopotassium phosphate ($KH_2PO_4$; 32 mM) and tripotassium phosphate ($K_3PO_4$; 18 mM) may be mixed to adjust a pH value to 7.

In addition, to mimic the brain metabolite, the following reagent (metabolite) may be added.

N-acetyl-Laspartic acid; Creatine hydrate; Cr; 10.0 mM, Choline chloride; Cho; 3.0 mM, Myo-inositol; NAA; 12.5 mM, L-Glutamic acid; Glu; 12.5 mM, DL-lactic acid; Lac; 5.0 mM, 4-Aminobutyric acid; GABA; 10.0 mM, mI; 7.5 mM, L-Alanine; Al; 10.0 mM, L-Glutamine; Gln; 12.5 mM, Taurine; Tau; 6.0 mM In addition, in order to evaluate quality assurance in accordance with the presence or absence of the artifacts at upper and lower ends of the first container 10a and the second container 10b, a quantitative accuracy analysis may be carried out by performing a voxel size test, a signal to noise ratio evaluation, a line width evaluation, a moisture suppression evaluation, and an evaluation of symmetry of moisture signals.

In addition, in a case in which images are obtained to correct a magnetic susceptibility artifact using the phantom 10 proposed by the present invention, it is possible to characterize magnetic susceptibility by analyzing how quickly the tissues is magnetized in a magnetic field and analyzing characteristic parts of the occurring artifact.

In addition, it is possible to differentiate signal dissipation and geometric distortion such as a boundary between air and water, a boundary between air and the Teflon, and a boundary between water and the Teflon, and to analyze information.

In addition, the correction of the artifact may be carried out by attachment to a ferromagnetic material by using the phantom 10 proposed by the present invention.

In the case of metal, such as a prosthesis and dental implants, which is greatly attracted to a magnet, geometric distortion in the magnetic resonance imaging may be obtained such as abnormal signals obtained in a frequency direction and changed signal intensity, for this reason, there is a problem in that image information may be changed.

However, the phantom 10 according to the present invention may correct the aforementioned problems by correcting the artifact with respect to metal and adjusting image protocol for the correction.

With the use of the phantom 10 proposed by the present invention, it is possible to propose performance evaluation information that enables image obtaining information of the computed tomography to be accurately obtained.

That is, image information of the computed tomography produces an intense signal in a case in which a high density material such as metal is included, and for this reason, there is a problem in that a value, which is absolutely different from an inherent computed tomography value (CT number, HU) that an actual treatment site has, is formed, and as a result, a dose is erroneously calculated during the radiotherapy.

The artifact has an effect not only on a diagnosis region but also on a treatment region, and it is necessary to recognize information about the presence or absence of the artifact when obtaining information and images of the metal and the prosthesis.

The subsequent error is that there is no method of restoring the values after image reconstruction is carried out because all of the values are changed when the reconstruction is carried out after the computed tomography; therefore, finding an actual true value may be difficult.

Therefore, with the use of the phantom 10 proposed by the present invention, it is possible to perform an alternative and an evaluation that may reduce the artifact through quality assurance before a diagnosis at the time of the computed tomography, and to perform imaging by correcting the protocol and the parameter.

According to the fusion phantom 10 for magnetic resonance imaging and computed tomography of the present invention, in order to reproduce an actual artifact at upper and lower ends based on the evaluation slice 21 for evaluating geometric cross section accuracy at the middle in the two spherical containers 10a and 10b, teeth extracted from patients and dental implants made of a titanium material, which is a biocompatible alloy currently used in dental clinics, may be inserted into the phantom.

Also, such material may be supplemented by a number of materials, an image of teeth of a child may be implemented, and additional insertion may be possible.

Typically, an ordinary person has 28 teeth except for wisdom teeth, and thus a material configured with non-limited teeth is to be inserted so that 14 upper teeth and 14 lower teeth may be implemented.

The teeth and the dental implants may be inserted in the middle of acrylic, so that they are possibly fixed, and attached, and desired teeth made of different substances may be inserted.

The teeth are made of thermoplastic resin so as to be fixed at a desired position.

The resin is inserted into the teeth retainers 11a and 11b by using advantages that the resin is easy to use because the resin is deformed by heat, and the resin may be deformed in a desired shape and a direction.

Accordingly, it is possible to completely make a retainer having a diameter of 1.5 cm and a height of 2 cm and a teeth model by surrounding the teeth, the dental implants, and the teeth made of a different material with the thermoplastic resin in a state in which the teeth, the dental implants, and the teeth made of a different material are deformed by heat, and by bringing the teeth, the dental implants, and the teeth made of a different material into close contact with the retainer.

A shape of the teeth retainer of the present invention may be modified, and an open mouth (a mouth is opened) and a closed mouth (the mouth is closed) may be implemented.

In addition, the present invention may not only perform a diagnosis, but also mimics a patient having a dental prosthesis during a radiotherapy, a patient having no dental prosthesis, a patient with an opened mouth, or a patient with a closed mouth.

According to a result of an experiment, it was determined that the thermoplastic resin for fixing the teeth have characteristics of substances of actual tissues of the human body, and thus may be suitable to use because the thermoplastic resin is a non-magnetic substance that does not have an effect on the process of obtaining magnetic resonance images.

In addition, according to the fusion phantom 10 for magnetic resonance imaging and computed tomography of the present invention, a column 20 made of a Teflon material, which may be used to check a slide position, is inserted into the two spherical containers 10a and 10b; therefore, it is possible to evaluate a position of a height of 2 cm at the teeth retainers 11a and 11b and a position of a height of 4 cm at the Teflon column 20.

In order to allow a voxel position to be freely set in the containers 10a and 10b, a metabolite quantitative evaluation is performed by setting a position at a hemispheric center and positioning the voxels at the upper and lower ends, and as a result, it is possible to simultaneously obtain the voxels at the upper and lower ends and improve temporal efficiency.

In addition, since a size of the phantom is similar to a size of the human brain, and the phantom is easy to evaluate the metabolite, and may reduce a chemical shift artifact due to a small acrylic thickness of 5 mm between the exterior and the interior.

In addition, a quantitative evaluation is enabled by using a single volume magnetic resonance spectroscopy.

That is, since adjusting the amount of metabolites at the upper and lower ends of the center of the hemispheres 10a and 10b may be possible, so that a desired signal is visible when obtaining spectrums by using the magnetic resonance spectroscopy, and it is possible to accurately measure position accuracy of a volume of interest (in particular, a voxel at a position closest to the exterior, a voxel at a position close to the Teflon, a voxel at a position close to the teeth, and a voxel at a position close to the dental implants), and for this reason, a change in chemical shift caused by the artifact may be evaluated.

Therefore, the phantom 10 for magnetic resonance imaging and computed tomography according to the present invention may accurately correct the artifact (in particular, the metallic artifact) and perform an analysis through various quantitative evaluations when evaluating performance of the magnetic resonance imaging system and the computed tomography system.

In comparison with the phantom in the related art, more accurate and various analysis of the metabolite may be possible, and performance maintenance of equipment and analysis functions are simultaneously visualized, and as a result, thereby obtaining images for a short period of time and improving reliability of equipment performance.

As described above, the detailed description of the exemplary embodiments of the present invention, which has been disclosed, is provided to enable those skilled in the art to implement and carry out the present invention. Although the exemplary embodiments of the present invention have been described in the above, it may be understood by those skilled in the art that the present invention may be variously modified and changed without departing from the scope of the present invention. For example, those skilled in the art may use the respective components disclosed in the aforementioned exemplary embodiments by combining the components. Therefore, the present invention is not intended to be limited to the exemplary embodiments disclosed herein, but intended to provide the widest scope that complies with the principles and the novel features disclosed herein.

The present invention may be specified as other aspects without departing from the spirit and the essential features of the present invention. Therefore, it should be appreciated that the detailed description is intended to be illustrative in every sense, and not restrictive. The scope of the present invention needs to be determined based on the reasonable interpretation of the appended claims, and all of the equivalent modifications of the present invention belong to the scope of the present invention. The present invention is not intended to be limited to the exemplary embodiments disclosed herein, but intended to provide the widest scope that complies with the principles and the novel features disclosed herein. In addition, an exemplary embodiment may be implemented by combining claims which are not clearly in a quotation relationship in the claims, and the claims may include new claims made by amendment after filing the application.

What is claimed is:

1. A phantom capable of simultaneously evaluating performance of magnetic resonance imaging (MRI) and computed tomography (CT), the phantom comprising:
a first hemispheric container; and
a second hemispheric container which has the same structure and the same size as the first container,
wherein the first container and the second container are connected by being in direct contact with each other so as to form a symmetrical structure, each of the first container and the second container includes a teeth retainer into which a plurality of teeth mimics, which mimics teeth of a body, is inserted, and an insertion hole into which at least one bone mimic is inserted, and an interior of each of the first container and the second container is filled with at least one solution that mimics a brain metabolite.

2. The phantom capable of simultaneously evaluating performance of MRI and CT of claim 1, wherein a first of first surface of the first container, which has a largest area, and a first of second surface of the second container having a largest area are in direct contact with each other so as to form a symmetrical structure, each of the first container and the second container further includes an inlet which is positioned at a side opposite to the first of first surface or the first of second surface such that at least one solution, which mimics the brain metabolite, is injected through the inlet, and the inlet is opened and closed by a closure.

3. The phantom capable of simultaneously evaluating performance of MRI and CT of claim 2, wherein the teeth retainers and the insertion holes are formed on the first of first surface and the first of second surface.

4. The phantom capable of simultaneously evaluating performance of MRI and CT of claim 1, wherein the interiors of the first container and the second container are filled with copper sulfate ($CuSO_4$; 0.7 g/L) first.

5. The phantom capable of simultaneously evaluating performance of MRI and CT of claim 4, wherein the interiors of the first container and the second container further include N-acetyl-Laspartic acid; Creatine hydrate; Cr; 10.0 mM, Choline chloride; Cho; 3.0 mM, Myo-inositol; NAA; 12.5 mM, L-Glutamic acid; Glu; 12.5 mM, DL-lactic acid; Lac; 5.0 mM, 4-Aminobutyric acid; GABA; 10.0 mM, mI; 7.5 mM, L-Alanine; Al; 10.0 mM, L-Glutamine; Gln; 12.5 mM, Taurine; Tau; 6.0 mM.

6. The phantom capable of simultaneously evaluating performance of MRI and CT of claim 1, wherein a mixture ratio between monopotassium phosphate ($KH_2PO_4$; 32 mM) and tripotassium phosphate ($K_3PO_4$; 18 mM) is adjusted to allow pH in the first container and the second container to be equal to pH of the body.

7. The phantom capable of simultaneously evaluating performance of MRI and CT of claim 1, wherein the plurality of teeth mimics include at least one of a titanium material and teeth.

8. The phantom capable of simultaneously evaluating performance of MRI and CT of claim 7, wherein the teeth retainer is made of a thermoplastic plastic material in order to fix a position of the plurality of inserted teeth mimics.

9. The phantom capable of simultaneously evaluating performance of MRI and CT of claim 8, wherein positions of the plurality of teeth mimics inserted into the teeth retainer are changeable by using a nature of the thermoplastic plastic in which the thermoplastic plastic is plastically deformed when the thermoplastic plastic is heated, and the thermoplastic plastic is reversibly hardened when the thermoplastic plastic is cooled.

10. The phantom capable of simultaneously evaluating performance of MRI and CT of claim 1, wherein fastening holes are formed in the first container and the second container, respectively, and the first container and the second container are connected by being in direct contact with each other by means of a coupler that penetrates the fastening holes.

* * * * *